(12) United States Patent
Nelson et al.

(10) Patent No.: US 11,834,523 B2
(45) Date of Patent: *Dec. 5, 2023

(54) NANOLIGNOCELLULOSE COMPOSITIONS AND PROCESSES TO PRODUCE THESE COMPOSITIONS

(71) Applicant: GranBio Intellectual Property Holdings, LLC, Minnetrista, MN (US)

(72) Inventors: Kimberly Nelson, Atlanta, GA (US); Theodora Retsina, Atlanta, GA (US)

(73) Assignee: GranBio Intellectual Property Holdings, LLC, Thomaston, GA (US)

( * ) Notice: Subject to any disclaimer, the term of this patent is extended or adjusted under 35 U.S.C. 154(b) by 116 days.

This patent is subject to a terminal disclaimer.

(21) Appl. No.: 17/142,525

(22) Filed: Jan. 6, 2021

(65) Prior Publication Data

US 2021/0221919 A1    Jul. 22, 2021

Related U.S. Application Data

(60) Division of application No. 16/014,589, filed on Jun. 21, 2018, now abandoned, which is a (Continued)

(51) Int. Cl.
  *D21C 1/02*    (2006.01)
  *D21C 9/00*    (2006.01)
  (Continued)

(52) U.S. Cl.
  CPC ............... *C08B 15/08* (2013.01); *C07G 1/00* (2013.01); *C08B 37/0057* (2013.01); *C08H 8/00* (2013.01);
  (Continued)

(58) Field of Classification Search
  CPC .......... C08B 15/08; D21C 1/02; D21C 9/007; D21H 11/18
  See application file for complete search history.

(56) References Cited

U.S. PATENT DOCUMENTS

| | | | |
|---|---|---|---|
| 9,322,133 B2 * | 4/2016 | Nelson ............ | C12P 7/56 |
| 11,359,334 B2 * | 6/2022 | Retsina ............ | D21C 9/007 |
| 2014/0249237 A1 * | 9/2014 | Ferraro ............ | C10G 2/32 |
| | | | 422/162 |

FOREIGN PATENT DOCUMENTS

| | | | | |
|---|---|---|---|---|
| JP | 2006136263 A | * | 6/2006 | |
| WO | WO-2014202354 A1 | * | 12/2014 | ............. C08B 15/08 |

OTHER PUBLICATIONS

McGovern et al., Experiments on Water and Steam Cooking of Aspen, Oct. 1949, TAPPI, 32, 440-448 (Year: 1949).*

(Continued)

*Primary Examiner* — Anthony Calandra
(74) *Attorney, Agent, or Firm* — O'Connor & Company; Ryan P. O'Connor

(57) ABSTRACT

Some variations provide a new nanolignocellulose composition comprising, on a bone-dry, ash-free, and acetyl-free basis, from 35 wt % to 80 wt % cellulose nanofibrils, cellulose microfibrils, or a combination thereof, from 15 wt % to 45 wt % lignin, and from 5 wt % to 20 wt % hemicelluloses. The hemicelluloses may contain xylan or mannan as the major component. Novel properties arise from the hemicellulose content that is intermediate between high hemicellulose content of raw biomass and low hemicellulose content of conventional nanocellulose. The nanolignocellulose composition is hydrophobic due to the presence of lignin. Processes for making and using the nanolignocellulose compositions are also described.

2 Claims, 6 Drawing Sheets

Related U.S. Application Data continuation-in-part of application No. 15/278,800, filed on Sep. 28, 2016, now abandoned.

(60) Provisional application No. 62/523,293, filed on Jun. 22, 2017, provisional application No. 62/235,052, filed on Sep. 30, 2015.

(51) Int. Cl.
*D21H 11/18* (2006.01)
*D21B 1/06* (2006.01)
*C08B 15/08* (2006.01)
*D21C 5/00* (2006.01)
*D21C 11/00* (2006.01)
*C08H 8/00* (2010.01)
*C12P 19/14* (2006.01)
*C12P 7/10* (2006.01)
*C12P 19/02* (2006.01)
*C07G 1/00* (2011.01)
*C08B 37/00* (2006.01)
*C09K 8/10* (2006.01)
*C09K 8/34* (2006.01)
*C09K 8/64* (2006.01)
*C09K 8/68* (2006.01)
*C13K 1/02* (2006.01)
*D21C 3/00* (2006.01)
*D21C 3/06* (2006.01)
*D21C 9/10* (2006.01)

(52) U.S. Cl.
CPC .................. *C09K 8/10* (2013.01); *C09K 8/34* (2013.01); *C09K 8/64* (2013.01); *C09K 8/68* (2013.01); *C12P 7/10* (2013.01); *C12P 19/02* (2013.01); *C12P 19/14* (2013.01); *C13K 1/02* (2013.01); *D21B 1/061* (2013.01); *D21C 1/02* (2013.01); *D21C 3/003* (2013.01); *D21C 3/006* (2013.01); *D21C 3/06* (2013.01); *D21C 5/005* (2013.01); *D21C 9/007* (2013.01); *D21C 9/10* (2013.01); *D21C 11/0007* (2013.01); *D21H 11/18* (2013.01)

(56) References Cited

OTHER PUBLICATIONS

Osong et al., Mechanical Pulp Based Nano-ligno-cellulose, 2014 Mid Sweden University (Year: 2014).*

* cited by examiner

NANOLIGNOCELLULOSE COMPOSITIONS AND PROCESSES TO PRODUCE THESE COMPOSITIONS

PRIORITY DATA

This patent application is a divisional application of U.S. patent application Ser. No. 16/014,589, filed on Jun. 21, 2018, which is (a) a continuation-in-part application of U.S. patent application Ser. No. 15/278,800, filed on Sep. 28, 2016 and (b) a non-provisional patent application of U.S. Provisional Patent App. No. 62/523,293, filed on Jun. 22, 2017, each of which is incorporated by reference herein. U.S. patent application Ser. No. 15/278,800 is a non-provisional patent application of U.S. Provisional Patent App. No. 62/235,052, filed on Sep. 30, 2015, which is incorporated by reference herein.

FIELD

The present invention generally relates to nanocellulose and related materials produced by fractionating lignocellulosic biomass and further processing the cellulose fraction.

BACKGROUND

Biomass refining (or biorefining) has become more prevalent in industry. Cellulose fibers and sugars, hemicellulose sugars, lignin, syngas, and derivatives of these intermediates are being utilized for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

Despite being the most available natural polymer on earth, it is only recently that cellulose has gained prominence as a nanostructured material, in the form of nanocrystalline cellulose (NCC), nanofibrillar cellulose (NFC), and bacterial cellulose (BC). Nanocellulose is being developed for use in a wide variety of applications such as polymer reinforcement, antimicrobial films, biodegradable food packaging, printing papers, pigments and inks, paper and board packaging, barrier films, adhesives, biocomposites, wound healing, pharmaceuticals and drug delivery, textiles, water-soluble polymers, construction materials, recyclable interior and structural components for the transportation industry, rheology modifiers, low-calorie food additives, cosmetics thickeners, pharmaceutical tablet binders, bioactive paper, pickering stabilizers for emulsion and particle stabilized foams, paint formulations, films for optical switching, and detergents.

Biomass-derived pulp may be converted to nanocellulose by mechanical processing. Although the process may be simple, disadvantages include high energy consumption, damage to fibers and particles due to intense mechanical treatment, and a broad distribution in fibril diameter and length.

Improved processes for producing nanocellulose from biomass at reduced energy costs are needed in the art. Also, improved starting materials (i.e., biomass-derived pulps) are needed in the art for producing nanocellulose. For some applications, it is desirable to produce nanocellulose with high hydrophobicity.

There is also a need in the art for increasing the strength of weak cellulose fibers, and improving certain properties of paper, corrugating medium pulp, and pulp products.

SUMMARY

Some variations provide a nanolignocellulose composition comprising, on a bone-dry, ash-free, and acetyl-free basis, from about 35 wt % to about 80 wt % cellulose nanofibrils, cellulose microfibrils, or a combination thereof, from about 15 wt % to about 45 wt % lignin, and from about 5 wt % to about 20 wt % hemicelluloses. The hemicelluloses may contain xylan or mannan as the major component.

In certain embodiments, the composition comprises from about 40 wt % to about 70 wt % cellulose nanofibrils, cellulose microfibrils, or a combination thereof on a bone-dry, ash-free, and acetyl-free basis.

In certain embodiments, the composition comprises from about 45 wt % to about 60 wt % cellulose nanofibrils, cellulose microfibrils, or a combination thereof on a bone-dry, ash-free, and acetyl-free basis.

In certain embodiments, the composition comprises from about 20 wt % to about 40 wt % lignin on a bone-dry, ash-free, and acetyl-free basis.

In certain embodiments, the composition comprises from about 25 wt % to about 35 wt % lignin on a bone-dry, ash-free, and acetyl-free basis.

In certain embodiments, the composition comprises from about 7 wt % to about 15 wt % hemicelluloses on a bone-dry, ash-free, and acetyl-free basis.

In certain embodiments, the composition comprises from about 8 wt % to about 14 wt % hemicelluloses on a bone-dry, ash-free, and acetyl-free basis.

In some embodiments, said nanolignocellulose composition is characterized by at least 99% filtration completion (such as 100% completion) in less than 100 minutes.

The present invention also provides a pulp product or a paper product containing a disclosed nanolignocellulose composition.

Some variations provide a process for producing a nanolignocellulose composition, the process comprising:
 (a) providing a lignocellulosic biomass feedstock;
 (b) digesting the feedstock with a reaction solution including steam and/or hot water in a digestor under effective reaction conditions to produce a digested stream containing cellulose-rich solids, hemicellulose oligomers, and lignin;
 (c) optionally washing the cellulose-rich solids to remove at least a portion of the hemicellulose oligomers and/or at least a portion of the lignin from the cellulose-rich solids;
 (d) mechanically treating the cellulose-rich solids to form a nanolignocellulose composition containing cellulose nanofibrils and/or cellulose nanocrystals, hemicelluloses, and lignin; and
 (e) recovering the nanolignocellulose composition.

In some processes, the nanolignocellulose composition comprises, on a bone-dry, ash-free, and acetyl-free basis, from about 35 wt % to about 80 wt % cellulose nanofibrils, cellulose microfibrils, or a combination thereof, from about 15 wt % to about 45 wt % lignin, and from about 5 wt % to about 20 wt % hemicelluloses.

In some processes, the nanolignocellulose composition is characterized by at least 99% filtration completion in less than 100 minutes.

The process may further include a pulp product or a paper product containing the nanolignocellulose composition. For example, the nanolignocellulose composition may be fed to a paper machine to produce a paper product.

DETAILED DESCRIPTION OF SOME EMBODIMENTS

Figure 1A:
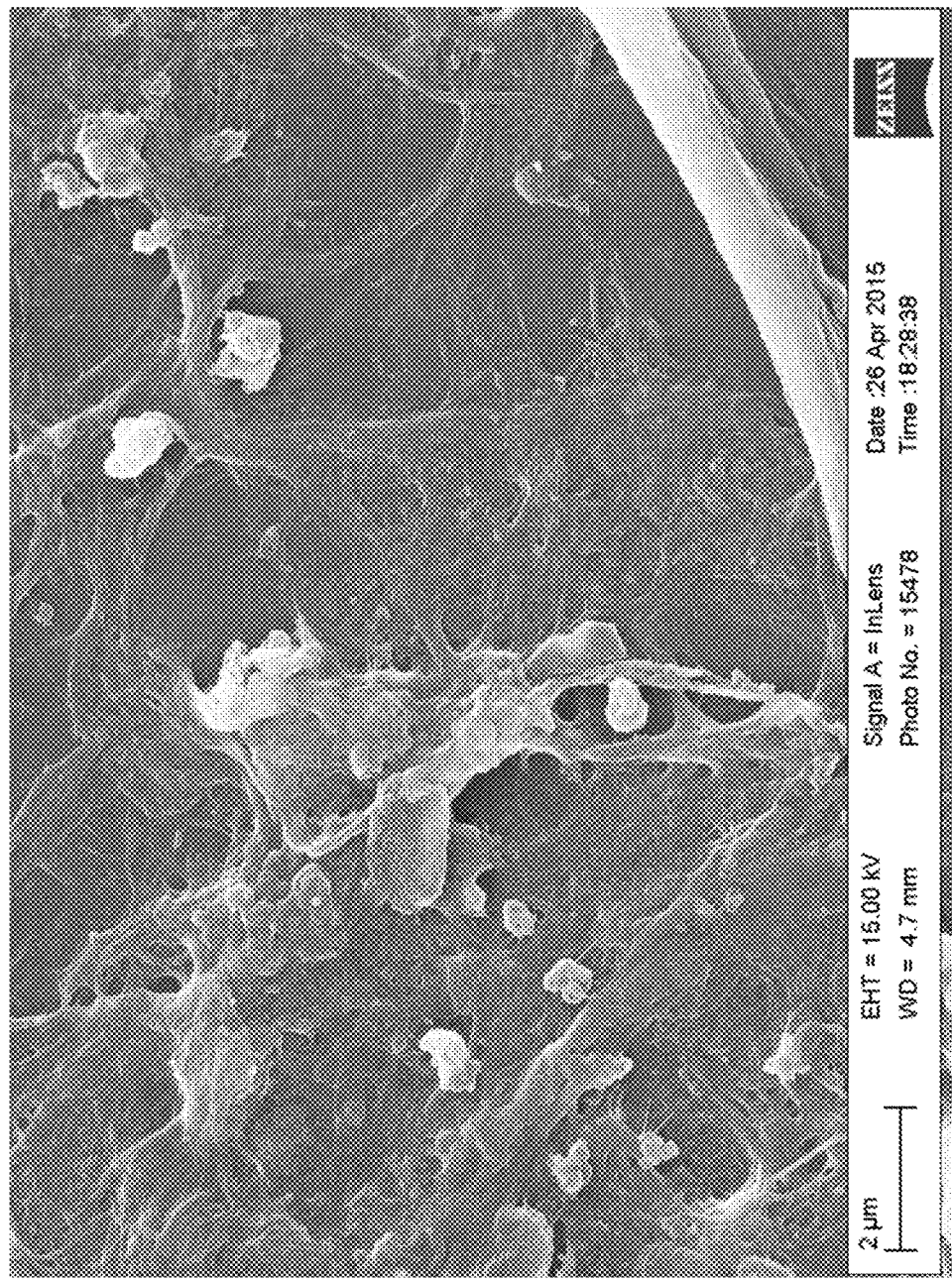
FIG. 1A is a SEM image of exemplary nanocellulose produced experimentally, by refining and homogenizing material produced from hot-water extraction of biomass.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Some variations are premised on the discovery of a surprisingly simple process for converting lignocellulosic biomass into nanocellulose or nanolignocellulose. Biomass may be subjected to a steam or hot-water soak to dissolved hemicelluloses. This step is followed by mechanical refining of the cellulose-rich (and lignin-rich) solids.

Some variations provide a nanolignocellulose composition comprising, on a bone-dry, ash-free, and acetyl-free basis, from about 35 wt % to about 80 wt % cellulose nanofibrils, cellulose microfibrils, or a combination thereof, from about 15 wt % to about 45 wt % lignin, and from about 5 wt % to about 20 wt % hemicelluloses.

In various embodiments, the nanolignocellulose composition may include about (or at least about, or at most about) 30, 35, 40, 45, 50, 55, 60, 65, 75, 75, 80, 85, or 90 wt % cellulose nanofibrils, cellulose microfibrils, or a combination thereof, a bone-dry, ash-free, and acetyl-free basis.

In various embodiments, the nanolignocellulose composition may include about (or at least about, or at most about) 10, 15, 20, 25, 30, 35, 40, 45, or 50 wt % lignin, a bone-dry, ash-free, and acetyl-free basis.

In various embodiments, the nanolignocellulose composition may include about (or at least about, or at most about) 2, 3, 4, 5, 6, 7, 8, 9, 10, 11, 12, 13, 14, 15, 16, 17, 18, 19, or 20 wt % hemicelluloses, a bone-dry, ash-free, and acetyl-free basis. The hemicelluloses may contain xylan or mannan as the major component.

A "bone-dry, ash-free, and acetyl-free basis" means that the recited concentrations are (i) absolutely free of any water, not including H—OH groups chemically contained, e.g. in sugar polymers; (ii) free of any ash, including both loose ash (e.g., sand or dirt) and bound ash (e.g., metal oxides that do not easily extract out of the solids); and (iii) acetyl groups bound to hemicellulose components, or free acetic acid derived from the acetyl groups.

In certain embodiments, the composition comprises from about 40 wt % to about 70 wt % cellulose nanofibrils, cellulose microfibrils, or a combination thereof on a bone-dry, ash-free, and acetyl-free basis.

In certain embodiments, the composition comprises from about 45 wt % to about 60 wt % cellulose nanofibrils, cellulose microfibrils, or a combination thereof on a bone-dry, ash-free, and acetyl-free basis.

In certain embodiments, the composition comprises from about 20 wt % to about 40 wt % lignin on a bone-dry, ash-free, and acetyl-free basis.

In certain embodiments, the composition comprises from about 25 wt % to about 35 wt % lignin on a bone-dry, ash-free, and acetyl-free basis.

In certain embodiments, the composition comprises from about 7 wt % to about 15 wt % hemicelluloses on a bone-dry, ash-free, and acetyl-free basis.

In certain embodiments, the composition comprises from about 8 wt % to about 14 wt % hemicelluloses on a bone-dry, ash-free, and acetyl-free basis.

The nanolignocellulose composition may contain water as moisture or in a slurry of solids, for example. The nanolignocellulose composition, on an ash-free and acetyl-free basis (but wet basis), may contain at least about (or at least about, or at most about) 5, 10, 15, 20, 25, 30, 35, 40, 45, 50, 60, 70, 80, 90 wt % water or higher.

The nanolignocellulose composition may contain ash. The nanolignocellulose composition, on a bone-dry and acetyl-free basis, may contain at least about (or at least about, or at most about) 0.1, 0.5, 1, 2, 3, 4, 5, wt % ash or higher.

The nanolignocellulose composition may contain acetyl groups. The nanolignocellulose composition, on a bone-dry and ash-free basis, may contain at least about (or at least about, or at most about) 0.1, 0.5, 1.0, 1.5, 2.0, 2.5, 3.0 wt % acetyl content or higher.

In some embodiments, said nanolignocellulose composition is characterized by at least 99% filtration completion (such as 100% completion) in less than 100 minutes.

The present invention also provides a pulp product or a paper product containing a disclosed nanolignocellulose composition.

In some variations, a paper mill co-produces nanolignocellulose and adds this material back to their own furnish as a way to make a stronger sheet, or a smoother sheet, or to enable cheaper furnish for the final paper product. In some embodiments, nanolignocellulose is produced using an existing low-consistency refiner, as a sideline operation at the mill or a nearby mill. At least some of the resulting nanolignocellulose is added back to the blend.

This concept may result in the ability to use lower-cost wood as the main feedstock to produce the pulp. Many paper mills use a blend of hardwoods and softwoods to achieve a desired combination of strength and sheet formation/smoothness. In addition to displacing higher-cost feedstocks, nanolignocellulose may act as a retention aid for the paper machines. Thus a paper machine may utilize the function of a retention aid and as well as sheet strength from the same material (nanolignocellulose).

The principles of the invention may be applied to any type of pulp or mill, including chemical (e.g., AVAP®, kraft, or sulfite), mechanical, thermomechanical, chemithermomechanical, hydrothermal-mechanical (e.g., GreenBox+® or GP3+™), or other types of pulping. Chemical pulping generally degrades the lignin and hemicellulose into small, water-soluble molecules which can be washed away from the cellulose fibers without depolymerizing the cellulose fibers. AVAP® pulping removes lignin and hemicelluloses without significant sugar degradation, allowing all major components (cellulose, hemicellulose, and lignin) to be recovered. The various mechanical pulping methods, such as groundwood and refiner mechanical pulping, physically tear the cellulose fibers from each other. Much of the lignin remains adhering to the fibers. Strength is impaired because the fibers may be cut. Related hybrid pulping methods use a combination of chemical and thermal treatment to begin an abbreviated chemical pulping process, followed by a mechanical treatment to separate the fibers. These hybrid methods include thermomechanical pulping and chemithermomechanical pulping. The chemical and thermal treatments reduce the amount of energy subsequently required by the mechanical treatment, and also reduce the amount of strength loss suffered by the fibers.

In some preferred embodiments, the invention is applied to a thermomechanical pulp mill or a hydrothermal-mechanical pulp mill.

In some embodiments, some of the thermomechanical or hydrothermal-mechanical pulp that is produced from the normal pulping operation is sent to a sideline nanocellulose production operation, involving mechanical refining of the thermomechanical or hydrothermal-mechanical pulp to generate nanocellulose particles (e.g., cellulose nanofibrils). Commonly owned U.S. patent application Ser. No. 15/278,800 filed 28 Sep. 2016, entitled "PROCESSES FOR PRODUCING NANOCELLULOSE, AND NANOCELLULOSE COMPOSITIONS PRODUCED THEREFROM," is hereby incorporated by reference herein for its teachings of converting thermomechanical or hydrothermal-mechanical pulp to nanocellulose, in some embodiments.

In some variations, nanocellulose may be added to corrugated medium pulp having inadequate strength properties, so that the resulting composite meets or exceeds the required strength properties for the intended application. While the principles of these embodiments are not limited to any particular source of corrugated medium or of nanocellulose, preferred embodiments combine corrugated medium produced by steam or hot-water extraction (known as GreenBox+® technology) with nanocellulose produced by refining pulp obtained by acidic solvent fractionation of biomass (known as AVAP® technology).

In some preferred embodiments, steam extraction or hot-water extraction of starting biomass is employed to produce pulp, which is then refined and optionally washed to produce corrugated medium pulp. Refer to commonly owned U.S. patent application Ser. No. 14/044,784 filed Oct. 2, 2013 (published as US 20140096922A1 on Apr. 10, 2014), which is hereby incorporated by reference herein, for exemplary process conditions to produce corrugated medium pulp, in various embodiments.

In some embodiments, hot-water extraction of starting biomass is employed to produce pulp, which is then refined to produce nanolignocellulose. As intended herein, "nanolignocellulose" is a material that contains particles of cellulose closely associated (i.e., chemically and/or physically) with substantial quantities of lignin and hemicellulose. The cellulose (within the nanolignocellulose particles) may include nanofibrils and/or microfibrils. The percentage of lignin (within the nanolignocellulose particles) is usually at least about 20 wt %, and the percentage of hemicellulose (within the nanolignocellulose particles) is usually at least about 5 wt %. Certain embodiments employ hot-water digestion and/or refining as described in commonly owned U.S. patent application Ser. No. 15/047,608, published as US 20160244788 on Aug. 25, 2016, which is hereby incorporated by reference herein.

Effective hot-water extraction conditions may include contacting the lignocellulosic biomass with steam (at various pressures in saturated, superheated, or supersaturated form) and/or hot water. In some embodiments, the HWE step is carried out using liquid hot water at a temperature from about 140-220° C., such as about 150° C., 160° C., 170° C., 175° C., 180° C., 185° C., 190° C., 200° C., or 210°

C. In some embodiments, the HWE step is carried out using liquid hot water with a residence time from about 1 minute to about 60 minutes, such as about 2, 2.5, 3, 3.5, 4, 5, 7.5, 10, 12.5, 15, 20, 25, 30, 35, 40, 45, 50, or 55 minutes.

In certain embodiments, lignin-coated nanocellulose (preferably lignin-coated cellulose nanofibrils) is added to corrugated medium pulp. Without being limited by theory, the lignin in the nanofibrils may reinforce the wet resistance of the corrugated medium paper. The production of lignin-coated nanocellulose is described in detail below. In some embodiments, lignin fills the voids between the fibers during pressing.

Using well-known techniques, corrugated medium product may be produced from the modified (with nanocellulose) corrugated medium pulp. See, for example, Twede and Selke, "Cartons, crates and corrugated board: handbook of paper and wood packaging technology," DEStech Publications, pages 41-56, 2005; and Foster, "Boxes, Corrugated" in The Wiley Encyclopedia of Packaging Technology, 1997, eds. Brody A and Marsh K, 2nd ed.

As intended herein, "nanocellulose" is broadly defined to include a range of cellulosic materials, including but not limited to microfibrillated cellulose (or cellulose microfibrils), nanofibrillated cellulose (or cellulose nanofibrils), microcrystalline cellulose, nanocrystalline cellulose, and particulated or fibrillated dissolving pulp. Typically, nanocellulose as provided herein will include particles having at least one length dimension (e.g., diameter) on the nanometer scale.

"Nanofibrillated cellulose" or equivalently "cellulose nanofibrils" means cellulose fibers or regions that contain nanometer-sized particles or fibers, or both micron-sized and nanometer-sized particles or fibers. "Nanocrystalline cellulose" or equivalently "cellulose nanocrystals" means cellulose particles, regions, or crystals that contain nanometer-sized domains, or both micron-sized and nanometer-sized domains. "Micron-sized" includes from 1 μm to 100 μm and "nanometer-sized" includes from 0.01 nm to 1000 nm (1 μm). Larger domains (including long fibers) may also be present in these materials.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for purposes of illustrating some embodiments only.

Some variations provide a pulp product comprising cellulose and nanolignocellulose, wherein the nanocellulose includes cellulose nanofibrils and/or cellulose nanocrystals, and wherein the nanolignocellulose is derived from the cellulose in a step that is separate from the pulping process to produce the cellulose.

In some embodiments, the pulping process is thermomechanical pulping or hydrothermal-mechanical pulping. The pulp product may be paper or a structural object (e.g., box, panel, engineered wood, etc.) different from paper.

In preferred embodiments, the pulp product is stronger than an otherwise-identical pulp product without the nanolignocellulose. In some embodiments, the pulp product is smoother than an otherwise-identical pulp product without the nanolignocellulose.

The pulping process is thermomechanical pulping, in certain embodiments, and the nanolignocellulose consists essentially of nanofibrils that contain cellulose, lignin, and hemicellulose. The nanofibrils may be produced by mechanically refining the cellulose precursor (with significant quantities of lignin and hemicelluloses) from thermomechanical pulping.

Other variations provide a corrugated medium pulp composition comprising cellulose pulp and nanolignocellulose, wherein the nanolignocellulose includes hydrophobic nanofibrils. In some embodiments, the nanolignocellulose is present in a concentration of at least about 0.1 wt %, 0.5 wt %, 1 wt %, 2 wt %, 5 wt %, or 10 wt % of the composition on a dry basis. In certain embodiments, nanolignocellulose is a significant portion of the pulp furnish, i.e. about 5 wt %, 10 wt %, 15 wt %, 20 wt %, 25 wt % or more.

In some embodiments of the corrugated medium pulp composition, the cellulose pulp is a mechanical pulp or a thermomechanical pulp (e.g., GreenBox+® pulp). In some embodiments, the cellulose pulp is a chemical pulp (e.g., AVAP®, kraft, sulfite, or soda pulp).

In some embodiments, the process further comprises producing a corrugated medium product from the corrugated medium pulp composition. The first amount of lignocellulosic biomass and the second amount of lignocellulosic biomass may be from the same source of biomass or different sources of biomass.

In some embodiments, the nanolignocellulose is lignin-containing hydrophobic cellulose. In these or other embodiments, the nanolignocellulose is predominantly in the form of nanofibrils, microfibrils, or a mixture thereof.

In some embodiments, a system is provided for carrying out the process as disclosed. The system may include a first sub-system to produce the first pulp at a first location and a second sub-system to produce the nanolignocellulose at a second location different from the first location. The production of the final product may be done at one of the first or second sub-systems, or at another location.

In some embodiments, the nanolignocellulose is derived from a biomass source selected from the group consisting of hardwoods, softwoods, agricultural residues, and combinations thereof.

In some embodiments, the nanolignocellulose is obtained from fractionating biomass in the presence of an acid, a solvent for lignin, and water, to generate cellulose-rich solids and a liquid phase; and then mechanically refining the cellulose-rich solids to generate the nanolignocellulose. In certain embodiments, the acid is sulfur dioxide and the solvent is ethanol. In certain embodiments, an AVAP® process is used to make nanolignocellulose for reinforcing cellulose fibers.

"Reinforcing" can be accomplished by simple mixing, grinding, milling, agitation, deposition/drying, or other treatments, in various embodiments.

In some embodiments, the method further comprises producing a single-fiber product from the cellulose fibers. In these or other embodiments, the method further comprises producing a composite from the cellulose fibers. Reinforcement of weak fibers with nanolignocellulose can increase the strength in composite and single fiber products, and other products.

In some embodiments, a product is made first from cellulose fibers, and then the product (not the pulp) is reinforced with nanolignocellulose. In these embodiments, if desired, the reinforcement can be made to the bulk product or to selected surfaces or regions, for example.

The biomass feedstock may be selected from hardwoods, softwoods, forest residues, eucalyptus, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, miscanthus, energy cane straw/residue, or combinations thereof. The process disclosed herein benefits from feedstock flexibility; it is effective for a wide variety of cellulose-containing feedstocks.

As used herein, "lignocellulosic biomass" means any material containing cellulose, lignin, and hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.). Various moisture levels may be associated with the starting biomass. The biomass feedstock need not be, but may be, relatively dry. In general, the biomass is in the form of a particulate or chip, but particle size is not critical in this invention.

In some embodiments, cellulose-rich solids are treated with a total mechanical energy of less than about 5000 kilowatt-hours per ton of the cellulose-rich solids, such as less than about 4000, 3000, 2000, or 1000 kilowatt-hours per ton of the cellulose-rich solids. Energy consumption may be measured in any other suitable units. An ammeter measuring current drawn by a motor driving the mechanical treatment device is one way to obtain an estimate of the total mechanical energy.

Mechanical treatment may employ one or more known techniques such as, but by no means limited to, milling, grinding, beating, sonicating, or any other means to form or release nanofibrils and/or nanocrystals in the cellulose. Essentially, any type of mill or device that physically separates fibers into fibrils may be utilized. Such mills are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp & Paper Technologists*, Tappi Press, 1992; and Hubbe et al., "Cellulose Nanocomposites: A Review," *BioResources* 3(3), 929-980 (2008).

The extent of mechanical treatment may be monitored during the process by any of several means. Certain optical instruments can provide continuous data relating to the fiber length distributions and % fines, either of which may be used to define endpoints for the mechanical treatment step. The time, temperature, and pressure may vary during mechanical treatment. For example, in some embodiments, sonication for a time from about 5 minutes to 2 hours, at ambient temperature and pressure, may be utilized.

In some embodiments, a portion of the cellulose-rich solids is converted to nanofibrils while the remainder of the cellulose-rich solids is not fibrillated. In various embodiments, about 10%, 20%, 30%, 40%, 50%, 60%, 70%, 80%, 90%, 95%, 99%, or substantially all of the cellulose-rich solids are fibrillated into nanofibrils. In some embodiments, a portion of the nanofibrils is converted to nanocrystals while the remainder of the nanofibrils is not converted to nanocrystals. During drying, it is possible for some nanocrystals to come back together and form nanofibrils.

Following mechanical treatment, the nanocellulose material may be classified by particle size. A portion of material may be subjected to a separate process, such as enzymatic hydrolysis to produce glucose. Such material may have good crystallinity, for example, but may not have desirable particle size or degree of polymerization.

The process may further comprise treatment of cellulose-rich solids with one or more enzymes or with one or more acids. When acids are employed, they may be selected from the group consisting of sulfur dioxide, sulfurous acid, lignosulfonic acid, acetic acid, formic acid, and combinations thereof. Acids associated with hemicellulose, such as acetic acid or uronic acids, may be employed, alone or in conjunction with other acids. Also, the process may include treatment of the cellulose-rich solids with heat. In some embodiments, the process does not employ any enzymes or acids.

When an acid is employed, the acid may be a strong acid such as sulfuric acid, nitric acid, or phosphoric acid, for example. Weaker acids may be employed, under more severe temperature and/or time. Enzymes that hydrolyze cellulose (i.e., cellulases) and possibly hemicellulose (i.e., with hemicellulase activity) may be employed, either instead of acids, or potentially in a sequential configuration before or after acidic hydrolysis.

In some embodiments, the process comprises enzymatically treating the cellulose-rich solids to hydrolyze amorphous cellulose. In other embodiments, or sequentially prior to or after enzymatic treatment, the process may comprise acid-treating the cellulose-rich solids to hydrolyze amorphous cellulose.

In some embodiments, the process further comprises enzymatically treating crystalline cellulose. In other embodiments, or sequentially prior to or after enzymatic treatment, the process further comprises acid-treating treating crystalline cellulose.

If desired, an enzymatic treatment may be employed prior to, or possibly simultaneously with, mechanical treatment. However, in preferred embodiments, no enzyme treatment is necessary to hydrolyze amorphous cellulose or weaken the structure of the fiber walls before isolation of nanofibers.

Following mechanical treatment, the nanolignocellulose may be recovered. Separation of cellulose nanofibrils and/or nanocrystals may be accomplished using apparatus capable of disintegrating the ultrastructure of the cell wall while preserving the integrity of the nanofibrils. For example, a homogenizer may be employed. In some embodiments, cellulose aggregate fibrils are recovered, having component fibrils in range of 1-100 nm width, wherein the fibrils have not been completely separated from each other.

In some embodiments, the nanolignocellulose material is characterized by an average length-to-width aspect ratio of particles from about 10 to about 1000, such as about 15, 20, 25, 35, 50, 75, 100, 150, 200, 250, 300, 400, or 500. Nanofibrils are generally associated with higher aspect ratios than nanocrystals. Nanocrystals, for example, may have a length range of about 100 nm to 500 nm and a diameter of about 1 to 10 nm. Nanofibrils may have a length of about 2000 nm and diameter range of 5 to 50 nm, translating to an aspect ratio of 40 to 400. In some embodiments, the aspect ratio is less than 50, less than 45, less than 40, less than 35, less than 30, less than 25, less than 20, less than 15, or less than 10.

Optionally, the process further comprises hydrolyzing amorphous cellulose into glucose, recovering the glucose, and fermenting the glucose to a fermentation product. Optionally, the process further comprises recovering, fermenting, or further treating hemicellulosic sugars derived from some of the hemicellulose. Optionally, the process further comprises recovering, combusting, or further treating the lignin.

Glucose that is generated from hydrolysis of amorphous cellulose may be integrated into an overall process to produce ethanol, or another fermentation co-product. Thus in some embodiments, the process further comprises hydrolyzing amorphous cellulose into glucose, and recovering the glucose. The glucose may be purified and sold. Or the glucose may be fermented to a fermentation product, such as but not limited to ethanol. The glucose or a fermentation product may be recycled to the front end, such as to hemicellulose sugar processing, if desired.

When hemicellulosic sugars are recovered and fermented, they may be fermented to produce a monomer or precursor thereof. The monomer may be polymerized to produce a polymer, which may then be combined with the nanocellulose material to form a polymer-nanocellulose composite.

In some embodiments, the process further comprises chemically converting the nanolignocellulose material to one or more nanolignocellulose derivatives. For example, nanolignocellulose derivatives may be selected from the group consisting of nanolignocellulose esters, nanolignocellulose ethers, nanolignocellulose ether esters, alkylated nanolignocellulose compounds, cross-linked nanolignocellulose compounds, acid-functionalized nanolignocellulose compounds, base-functionalized nanolignocellulose compounds, and combinations thereof.

Various types of nanolignocellulose functionalization or derivatization may be employed, such as functionalization using polymers, chemical surface modification, functionalization using nanoparticles (i.e. other nanoparticles besides the nanolignocellulose), modification with inorganics or surfactants, or biochemical modification.

High loading rates of lignin have been achieved in thermoplastics. Even higher loading levels are obtained with well-known modifications of lignin. The preparation of useful polymeric materials containing a substantial amount of lignin has been the subject of investigations for more than thirty years. Typically, lignin may be blended into polyolefins or polyesters by extrusion up to 25-40 wt % while satisfying mechanical characteristics. In order to increase the compatibility between lignin and other hydrophobic polymers, different approaches have been used. For example, chemical modification of lignin may be accomplished through esterification with long-chain fatty acids.

A significant factor limiting the application of strength-enhancing, lightweight nanocellulose in composites is cellulose's inherent hydrophilicity. Surface modification of the nanocellulose surface to impart hydrophobicity to enable uniform dispersion in a hydrophobic polymer matrix is an active area of study. It has been discovered that nanolignocellulose, as provided herein, is hydrophobic.

Optionally, the process for producing a hydrophobic nanolignocellulose material may further include chemically modifying the lignin to increase hydrophobicity of the nanolignocellulose material. Any known chemical modifications may be carried out on the lignin, to further increase the hydrophobic nature of the nanolignocellulose material provided by embodiments of this invention.

Some variations of the present invention are premised on relatively simple processes to generate high-viscosity compounds made from cellulosic biomass. The high-viscosity compounds will act as rheology modifiers when mixed in small proportions with different fluids, such as drilling fluids, paints, etc.

In hydraulic fracturing fluid formulations, particularly water-based formulations but also for oil-based formulations, these compositions may function as gelling agents. Easy mixing and handling allows for customization for each reservoir characteristics. Several properties of these rheology modifiers present strong advantages when compared to current available products on the market. Some of these properties are higher thermal stability, strong shear thinning, thixotropic qualities, and water solubility. Another important property of these new compounds is that they are biodegradable, and their production does not involve any chemicals other than biomass and water.

Some variations provide a process for producing a nanocellulose material, the process comprising:
   (a) providing a lignocellulosic biomass feedstock;
   (b) digesting the feedstock with a reaction solution including steam and/or hot water in a digestor under effective reaction conditions to produce a digested stream containing cellulose-rich solids, hemicellulose oligomers, and lignin;
   (c) optionally washing the cellulose-rich solids to remove at least a portion of the hemicellulose oligomers and/or at least a portion of the lignin from the cellulose-rich solids;
   (d) mechanically treating the cellulose-rich solids to form a nanocellulose material containing cellulose nanofibrils and/or cellulose nanocrystals; and
   (e) recovering the nanocellulose material.

The process may further include treatment of the cellulose-rich solids with one or more enzymes (e.g., cellulases) or with one or more acids, such as sulfur dioxide, sulfurous acid, lignosulfonic acid, acetic acid, formic acid, or combinations thereof. The process may further include treatment of the cellulose-rich solids with heat. In some embodiments, steps (b)-(d) do not employ any enzymes or externally added acids.

Figure 1B:
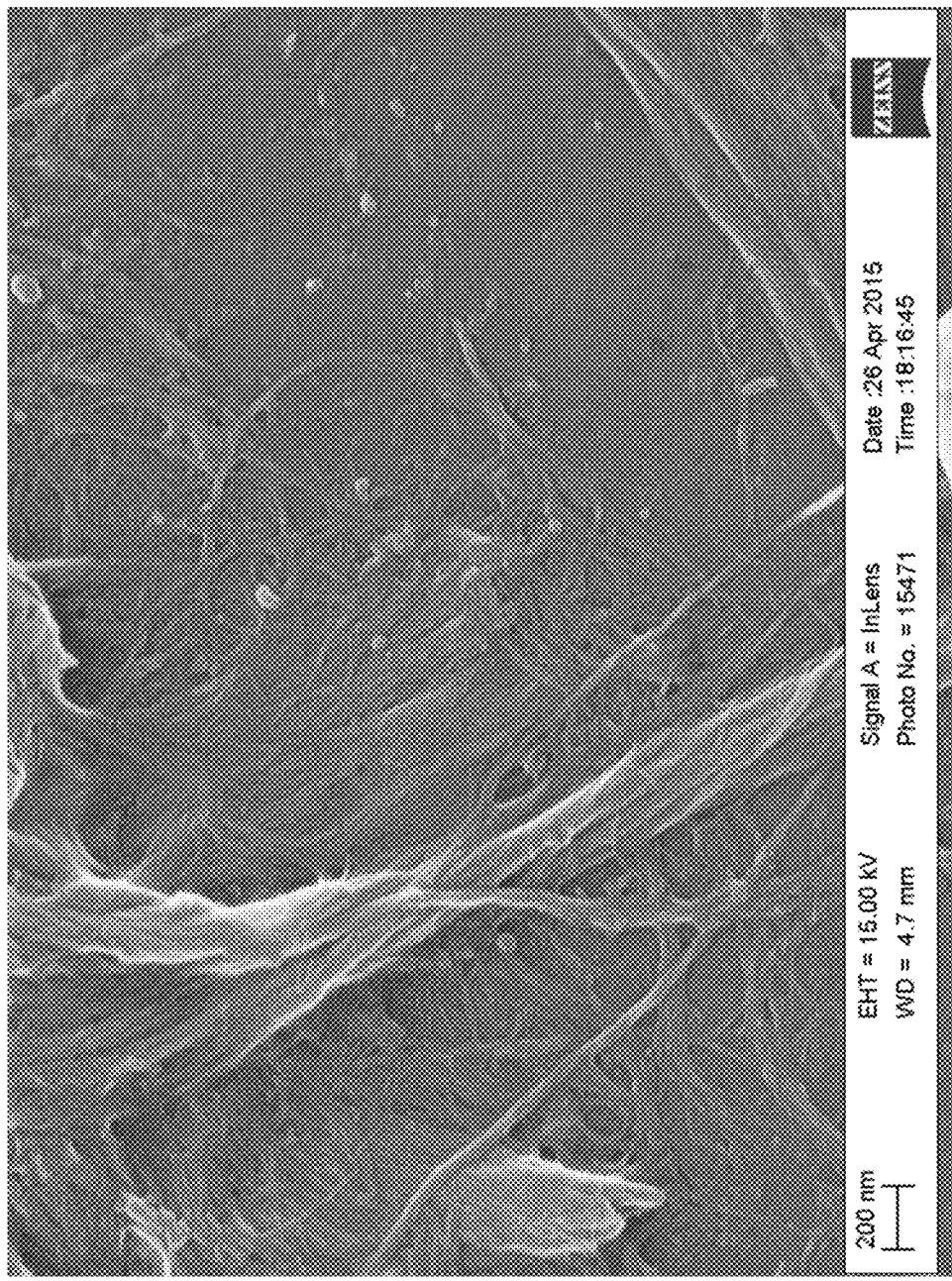
FIG. 1B is a SEM image of exemplary nanocellulose produced experimentally, by refining and homogenizing material produced from hot-water extraction of biomass.
Figure 1C:
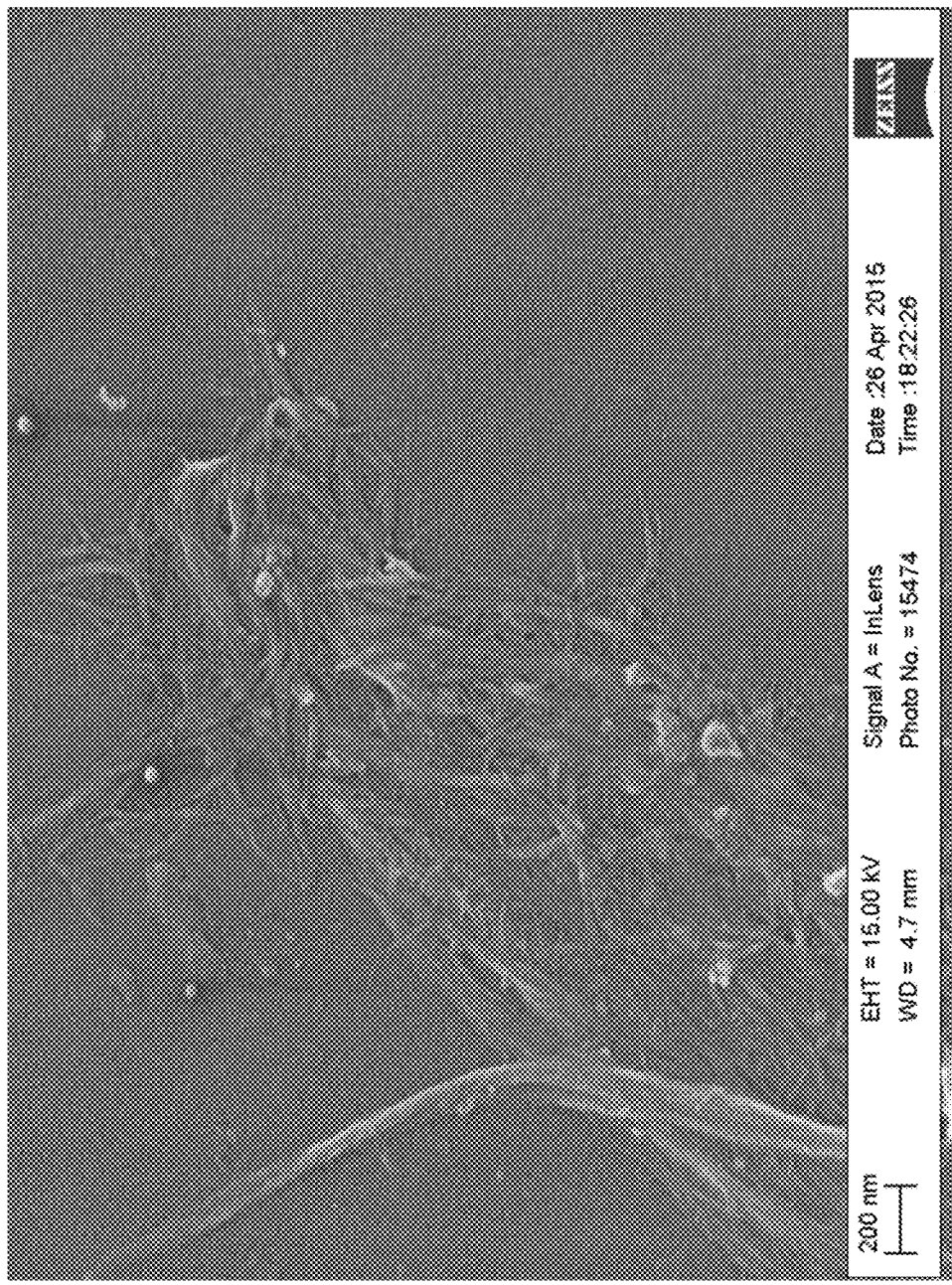
FIG. 1C is a SEM image of exemplary nanocellulose produced experimentally, by refining and homogenizing material produced from hot-water extraction of biomass.

The nanocellulose material may include cellulose nanofibrils or a mixture of cellulose nanofibrils and cellulose nanocrystals. FIGS. 1A-1C show SEM images of exemplary nanocellulose produced experimentally, by refining and homogenizing material produced from hot-water extraction of biomass. The nanocellulose material may also include lignin, including lignin particles less than 1 micron in diameter. The process may include bleaching the cellulose-rich solids and/or bleaching the nanocellulose material after it is produced.

In some embodiments, the process further comprises recovering, fermenting, or further treating hemicellulosic sugars derived from the hemicellulose oligomers. For example, the hemicellulosic sugars may be fermented to a fermentation product, such as (but not limited to) ethanol.

In some embodiments, the process further comprises hydrolyzing a portion of the cellulose-rich solids into glucose, recovering the glucose, and optionally fermenting the glucose to a fermentation product, such as n-butanol or 1,4-butanediol.

The process may further include recovering, combusting, or further treating the lignin that is washed from the cellulose-rich solids. Some or all of the initial lignin (in the starting feedstock) may become part of the nanocellulose material, which will be at least partially hydrophobic due to the presence of the lignin.

In some embodiments, the process further comprises chemically converting the nanocellulose material to one or more nanocellulose derivatives. For example, nanocellulose derivatives may be selected from the group consisting of nanocellulose esters, nanocellulose ethers, nanocellulose ether esters, alkylated nanocellulose compounds, cross-linked nanocellulose compounds, acid-functionalized nanocellulose compounds, base-functionalized nanocellulose compounds, and combinations thereof.

In certain embodiments, step (d) includes disk refining followed by homogenization of the cellulose-rich solids. Step (d), or a portion thereof, may be conducted at a solids consistency of at least 10 wt %, such as at least 20 wt %.

The process includes, in some embodiments, exploding cellulose fibers contained in the cellulose-rich solids. The exploding of fibers may be achieved using steam explosion and/or rapid pressure reduction, for example. In certain embodiments, step (d) utilizes a blow-line refiner, optionally with pressure reduction.

Some variations of the invention provide a process for producing a biomass-derived rheology modifier from cellulosic biomass, the process comprising:
(a) providing a feedstock comprising cellulosic biomass;
(b) digesting the feedstock with a reaction solution including steam and/or hot water in a digestor under effective reaction conditions to produce a digested stream containing cellulose-rich solids, hemicellulose oligomers, and lignin;
(c) refining the cellulose-rich solids in a first high-intensity refining unit, thereby generating refined cellulose solids;
(d) washing the refined cellulose solids following step (c), and/or washing the digested stream prior to step (c) followed by the refining, thereby generating washed refined cellulose solids;
(e) gelling the washed refined cellulose solids in a second high-intensity refining unit, thereby generating gelled cellulose solids; and
(f) homogenizing the gelled cellulose solids in a high-shear homogenizer, thereby generating a biomass-derived rheology modifier containing cellulose nanofibrils, cellulose nanocrystals, or a mixture of cellulose nanofibrils and cellulose nanocrystals.

Optionally, the process further comprises wet or dry cleaning the feedstock prior to step (b). Optionally, whether or not the feedstock is cleaned, the process further comprises reducing size of the feedstock prior to step (b).

Step (b) may be conducted at a digestion temperature from about 140° C. to about 210° C. Step (b) may be conducted for a digestion time from about 5 minutes to about 45 minutes. Step (b) may be conducted at a liquid/solid weight ratio from about 2 to about 6.

The process may include a hot-blow or cold-blow pressure reduction of the digested stream, following step (b).

The first high-intensity refining unit may utilize disks or a conical plate, for example. In various embodiments, the first high-intensity refining unit transfers energy to the cellulose-rich solids in an amount from about 20 kW/ton to about 200 kW/ton (bone-dry basis).

Washing in step (d) may be conducted at a temperature from about 18° C. to about 95° C. In some embodiments, washing in step (d) utilizes a pressurized screw press.

The second high-intensity refining unit may utilize disks or a conical plate, for example. The first and second high-intensity refining units preferably have different patterns with different groove and dam dimensions. In various embodiments, the second high-intensity refining unit transfers energy to the washed refined cellulose solids in an amount from about 20 kW/ton to about 200 kW/ton (bone-dry basis).

In some embodiments, the high-shear homogenizer transfers a shear force equivalent to a shear force produced under a pressure from about 10,000 psig to about 25,000 psig.

In some embodiments, the washed refined cellulose solids are stored for a period of time prior to step (e). Step (e) may be conducted at a different location than steps (a)-(d). Also, step (f) may be conducted at a different location than steps (a)-(e).

Other variations of the invention provide a process for producing a biomass-derived rheology modifier from cellulosic biomass, the process comprising:
(a) providing a pretreated feedstock comprising cellulose-rich solids;
(b) refining the cellulose-rich solids in a first high-intensity refining unit, thereby generating refined cellulose solids;
(c) optionally washing the refined cellulose solids following step (b), and/or optionally washing the digested stream prior to step (b) followed by the refining, thereby generating washed refined cellulose solids;
(d) gelling the washed refined cellulose solids in a second high-intensity refining unit, thereby generating gelled cellulose solids; and
(e) homogenizing the gelled cellulose solids in a high-shear homogenizer, thereby generating a biomass-derived rheology modifier containing cellulose nanofibrils.

In some embodiments, the pretreated feedstock is kraft pulp derived from wood or lignocellulosic biomass. In some embodiments, the pretreated feedstock is sulfite pulp derived from wood or lignocellulosic biomass. In some embodiments, the pretreated feedstock is soda pulp derived from wood or lignocellulosic biomass. In some embodiments, the pretreated feedstock is mechanical pulp derived from wood or lignocellulosic biomass. In some embodiments, the pretreated feedstock is thermomechanical pulp derived from wood or lignocellulosic biomass. In some embodiments, the pretreated feedstock is chemimechanical pulp derived from wood or lignocellulosic biomass.

Variations of the invention provide a water-based hydraulic fracturing fluid formulation or additive comprising (i) a nanocellulose material produced in accordance with a process as described or (ii) a biomass-derived rheology modifier produced in accordance with a process as described.

Variations of the invention provide an oil-based hydraulic fracturing fluid formulation or additive comprising (i) a nanocellulose material produced in accordance with the process as described or (ii) a biomass-derived rheology modifier produced in accordance with the process as described.

Variations of the invention provide a water-based drilling fluid formulation or additive comprising (i) a nanocellulose material produced in accordance with the process as described or (ii) a biomass-derived rheology modifier produced in accordance with the process as described.

Variations of the invention provide an oil-based drilling fluid formulation or additive comprising (i) a nanocellulose material produced in accordance with the process as described or (ii) a biomass-derived rheology modifier produced in accordance with the process as described.

Some variations provide a polymer-nanocellulose composite comprising (i) a nanocellulose material produced in accordance with the process as described or (ii) a biomass-derived rheology modifier produced in accordance with the process as described. Exemplary polymers include, but are not limited to, polylactide, poly(vinyl alcohol), polyethylene, polypropylene, etc.

In some embodiments, this process creates high-viscosity compounds with size between 1 micron and 100 microns, such as between 15 micron and 50 microns. These new compounds produced without any chemicals (other than biomass and water) may be used as rheology modifiers and, being based on cellulose, are fully biodegradable.

The process presents several advantages. The design allows the process to be fully integrated in one line from the startup with the biomass through production of the high-viscosity compounds. Or the process could be separated in several modules which could be located at different geographical sites.

The biomass feedstock may be selected from hardwoods, softwoods, forest residues, agricultural residues (such as sugarcane bagasse), industrial wastes, consumer wastes, or combinations thereof. In any of these processes, the feedstock may include sucrose. In some embodiments with sucrose present in the feedstock, a majority of the sucrose is recovered as part of the fermentable sugars.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof. In certain embodiments, the agricultural residue is sugarcane bagasse, energy cane bagasse, sugarcane straw, or energy cane straw.

In some embodiments, the process further comprises wet or dry cleaning the feedstock prior to step (b). In some embodiments, the process further comprises reducing size of the feedstock prior to step (b). The process may include size reduction, hot-water soaking, dewatering, steaming, or other operations, upstream of the digestor.

Step (b) may be conducted at a digestion temperature from about 140° C. to about 210° C., such as from about 175° C. to about 195° C. Step (b) may be conducted for a digestion time from about 5 minutes to about 45 minutes, such as from about 15 minutes to about 30 minutes. Step (b) may be conducted at a liquid/solid weight ratio from about 2 to about 6, such as about 3, 3.5, 4, 4.5, or 5.

In some embodiments, the reaction solution comprises steam in saturated, superheated, or supersaturated form. In some embodiments, the reaction solution comprises hot water.

The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The solid-phase residence time for the digestor (pressurized extraction vessel) may vary from about 2 minutes to about 4 hours, such as about 5 minutes to about 1 hour. In certain embodiments, the digestor residence time is controlled to be about 5 to 15 minutes, such as 5, 6, 7, 8, 9, 10, 11, 12, 13, 14 or 15 minutes. The liquid-phase residence time for the digestor may vary from about 2 minutes to about 4 hours, such as about 5 minutes to about 1 hour. The vapor-phase residence time for the digestor may vary from about 1 minute to about 2 hours, for example, such as about 3 minutes to about 30 minutes. The solid-phase, liquid-phase, and vapor-phase residence times may all be about the same, or they may be independently controlled according to reactor-engineering principles (e.g., recycling and internal recirculation strategies).

In some embodiments, the process further comprises a hot-blow pressure reduction of the digested stream, following step (b). Alternatively, a cold-blow pressure reduction of the digested stream, following step (b), may be employed.

To reduce pressure, a blow tank may be situated between the digestor and the refining unit. In some embodiments, vapor is separated from the blow tank, and heat is recovered from at least some of the vapor. Optionally, at least some of the vapor is compressed and returned to the digestor, and/or at least some of the vapor is purged from the process. Note that "blow tank" should be broadly construed to include not only a tank but any other apparatus or equipment capable of allowing a pressure reduction in the process stream. Thus a blow tank (or blow means) may be a tank, vessel, section of pipe, valve, separation device, or other unit.

Each mechanical refiner may be selected from the group consisting of a hot-blow refiner, a hot-stock refiner, a disk refiner, a conical refiner, a cylindrical refiner, an in-line defibrator, a homogenizer, and combinations thereof. Mechanically treating (refining) may employ one or more known techniques such as, but by no means limited to, milling, grinding, beating, sonicating, or any other means to reduce cellulose particle size. Such refiners are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp & Paper Technologists*, Tappi Press, 1992.

The refining may be conducted at a wide range of solids concentrations (consistency), including from about 2% to about 50% consistency, such as about 3%, 4%, 5%, 6%, 7%, 8%, 9%, 10%, 11%, 12%, 15%, 20%, 30%, 35%, or 40% consistency.

Each mechanical refiner may be configured to transfer from about 20 to about 200 kW/ton (i.e., kW refining power per ton fiber, based on the solid phase that is converted to the refined stream). In certain embodiments, the mechanical refiner is configured to transfer from about 75 to about 150 kW refining power per ton fiber. For example, a mechanical refiner with plates may be adjusted by changing the plate type, gap, speed, etc. to achieve these power inputs.

The extent of mechanical treatment may be monitored during the process by any of several means. Certain optical instruments can provide continuous data relating to the fiber length distributions and % fines, either of which may be used to define endpoints for the mechanical treatment step. The time, temperature, and pressure may vary during mechanical treatment. For example, in some embodiments, sonication for a time from about 5 minutes to 2 hours, at ambient temperature and pressure, may be utilized.

In some embodiments, a portion of the cellulose-rich solids is converted to fibrillated and/or gelled while the remainder of the cellulose-rich solids is not fibrillated and/or gelled. In various embodiments, about 10%, 20%, 30%, 40%, 50%, 60%, 70%, 80%, 90%, 95%, 99%, or substantially all of the cellulose-rich solids are fibrillated and/or gelled.

The first high-intensity refining unit may utilize disks or a conical plate, for example. In some embodiments, the first high-intensity refining unit transfers energy to the cellulose-rich solids in an amount from about 20 kW/ton to about 200 kW/ton (bone-dry basis), such as from about 75 kW/ton to about 150 kW/ton (bone-dry basis).

In some embodiments, washing in step (d) is conducted at a temperature from about 18° C. to about 95° C., such as from about 70° C. to about 80° C. Washing in step (d) may utilize a pressurized screw press.

In some embodiments, the second high-intensity refining unit utilizes disks or a conical plate. The first and second high-intensity refining units preferably have different patterns with different groove and dam dimensions. In some embodiments, the second high-intensity refining unit transfers energy to the washed refined cellulose solids in an amount from about 20 kW/ton to about 200 kW/ton (bone-dry basis), such as from about 75 kW/ton to about 150 kW/ton (bone-dry basis).

In some embodiments, the high-shear homogenizer (or other unit operation capable of imparting shear) transfers a shear force equivalent to a shear force produced under a pressure from about 1,000 psig to about 50,000 psig, such as about 10,000 psig to about 25,000 psig.

The washed refined cellulose solids may be stored for a period of time prior to step (e), which may be conducted at a different location than steps (a)-(d). In some embodiments, not step (f) is conducted at a different location than steps (a)-(e).

In some embodiments, the biomass-derived rheology modifier may be characterized by a particle size (e.g., fiber or fibril length or effective length) from about 1 microns to about 100 microns, such as from about 1 micron to about 50 microns. In certain embodiments, a majority (such as about 50%, 60%, 70%, 80%, 90%, or 95%) of the particles are in the size range of 10-15 microns. The biomass-derived rheology modifier may include particles smaller than 5 microns, such as 4, 3, 2, 1 micron or less (i.e. nanoparticles). The width of the particles may be less than 1 micron. Particles larger than 100 microns, such as 150, 200, 250, 300, 400, 500 microns or greater, may be present.

In some embodiments, the biomass-derived rheology modifier may be characterized by a particle size (e.g., length or effective length) less than about 10 microns, such as about 9, 8, 7, 6, 5, 4, 3, 2, 1 micron or less. In certain embodiments, the nanocellulose particle length is about 900, 800, 700, 600, 500, 400, 300, 200, 100 nm or less. In these or other embodiments (including lengths in excess of 1 micron), the nanocellulose particle diameter may be from about 3 nm to about 1000 nm, such as from about 5 nm to about 500 nm, or about 10 nm to about 200 nm or about 5, 10, 15, 20, 25, 30, 40, 50, 60, 70, 80, 90, 100, 150, 200, 250, 300, 350, 400, or 450 nm. In some of these embodiments, the nanoparticles (or a portion of them) may be characterized as nanocrystals.

The rheology modifier compounds are primarily cellulose-based polymers, with some microcrystalline shape like nanocellulose including some of the initial biomass lignin in the structure. In some embodiments, the compound properties are predominantly hydrophilic, allowing a strong stability of water-based drilling fluid and water-based fracking fluids. In some embodiments with lignin content and suitable high-intensity refining, the compounds are hydrophobic, moderately hydrophobic, or a combination of hydrophilic and hydrophobic.

The present disclosure provides a water-based hydraulic fracturing fluid formulation or additive comprising a biomass-derived rheology modifier produced in accordance with the processes described herein.

The present disclosure provides an oil-based hydraulic fracturing fluid formulation or additive comprising a biomass-derived rheology modifier produced in accordance with the processes described herein.

The present disclosure provides a water-based drilling fluid formulation or additive comprising a biomass-derived rheology modifier produced in accordance with the processes described herein.

The present disclosure provides an oil-based drilling fluid formulation or additive comprising a biomass-derived rheology modifier produced in accordance with the processes described herein.

The process may further include removal of one or more fermentation inhibitors (such as acetic acid or furfural) by stripping. This stripping may be conducted by treating the hydrolyzed cellulose stream, prior to fermentation. Alternatively, or additionally, the stripping may be conducted on a stream following digestion, such as in the blow line.

The process in some embodiments further comprises a step of fermenting the fermentable sugars, contained in the liquid phase derived from the initial digestion, to a dilute fermentation product. The process further may comprise concentration and purification of the fermentation product. The fermentation product may be selected from ethanol, n-butanol, 1,4-butanediol, succinic acid, lactic acid, or combinations thereof, for example. Also, a solid stream containing lignin may be removed, either prior to fermentation or downstream of fermentation.

A step may include conditioning of hydrolysate to remove some or most of the volatile acids and other fermentation inhibitors. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) to assist in the removal of hemicelluloses or minerals from the biomass. This recycle of organic acids, such as acetic acid, may be optimized along with process conditions that may vary depending on the amount recycled, to improve the cooking effectiveness.

A step may include recovering fermentable sugars, which may be stored, transported, or processed. A step may include fermenting the fermentable sugars to a co-product (the primary product being rheology modifiers).

A step may include preparing solid residuals (containing lignin) for combustion. This step may include refining, milling, fluidizing, compacting, and/or pelletizing the dried, extracted biomass. The solid residuals may be fed to a boiler in the form of fine powder, loose fiber, pellets, briquettes, extrudates, or any other suitable form. Using known equipment, solid residuals may be extruded through a pressurized chamber to form uniformly sized pellets or briquettes.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning, after concentration of the distillation bottoms.

Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

The process may be continuous, semi-continuous, or batch. When continuous or semi-continuous, the stripping column may be operated countercurrently, cocurrently, or a combination thereof.

The process may further comprise bleaching the cellulose-rich solids prior to a refining step and/or as part of refining. Alternatively, or additionally, the process may further comprise bleaching the refined material, the gelled material, or the homogenized material. Any known bleaching technology or sequence may be employed, including enzymatic bleaching.

Rheology modifiers as provided herein may be incorporated into drilling fluids, drilling fluid additives, fracturing fluids, and fracturing fluid additives. The rheology modifiers may be present in a wide variety of concentrations, such as from about 0.001 wt % to about 10 wt % or higher, e.g. about 0.01 wt %, 0.05 wt %, 0.1 wt %, 0.5 wt %, 1 wt %, or 2 wt %.

The invention, in some variations, is related to a group of cellulosic compounds which could be used in different applications. One of the applications is to use them as product enhancers of drilling fluids. The rheology modifiers may serve one or more functions in drilling fluids. For example, the rheology modifier may serve as a gelling agent to increase viscosity, or a viscosifier in general. The rheology modifier may serve as a friction reducer. Also, rheology modifiers may be a drilling polymer, displacing other polymers or adding to them.

Drilling fluids are fluids used in drilling in the natural gas and oil industries, as well as other industries that use large drilling equipment. The drilling fluids are used to lubricate, provide hydrostatic pressure, keep the drill cool, and keep the hole as clean as possible of drill cuttings. Rheology modifiers provided herein are suitable as additives to these drilling fluids.

In some embodiments, enzymes can be used as a "breaker" with the compositions, to break down rheology modifiers after some period of time or under certain conditions (e.g., temperature or pH).

In some embodiments, lignosulfonates are incorporated for enhanced lubricity in drilling applications. Also, the ability of lignosulfonates to reduce the viscosity of mineral slurries can be beneficial in oil drilling muds.

In some embodiments, native lignin or non-sulfonated lignin, or non-sulfonated lignin derivatives, are incorporated into the compositions.

Some embodiments provide a drilling fluid additive comprising rheology modifiers.

Some embodiments provide a drilling fluid additive comprising rheology modifiers, wherein the additive further comprises lignosulfonates.

Some embodiments provide a drilling fluid additive comprising rheology modifiers, wherein the additive further comprises non-sulfonated lignin.

Some embodiments provide a drilling fluid additive comprising rheology modifiers, wherein the additive further comprises a crosslinking agent.

Some embodiments provide a drilling fluid additive comprising crosslinked rheology modifiers and lignosulfonates.

Some embodiments provide drilling fluids comprising the drilling fluid additives as disclosed. The drilling fluid may be a water-based drilling fluid, an oil-based drilling fluid, or a hybrid water-based/oil-based drilling fluid.

In various embodiments, the drilling fluid further comprises one or more of a biomass-derived weighting material, a biomass-derived filtration-control agent, a biomass-derived rheology-control agent, a biomass-derived pH-control agent, a biomass-derived lost-circulation material, a biomass-derived surface-activity modifier, a biomass-derived lubricant, and a biomass-derived flocculant, and/or a biomass-derived stabilizer.

In some variations, the invention provides a method of using a drilling fluid additive, the method comprising combining a drilling fluid additive as disclosed into a base fluid to generate a drilling fluid. In some variations, the invention provides a method comprising introducing a disclosed drilling fluid additive directly or indirectly into a geological formation.

In some variations, a method of drilling includes introducing a drilling fluid additive directly or indirectly into a geological formation, wherein the drilling fluid additive includes an enzyme for degelling under effective conditions. In related variations, a method of drilling includes introducing a drilling fluid additive directly or indirectly into a geological formation, and then later introducing an enzyme for degelling under effective conditions.

Some variations provide a process for producing a drilling fluid additive, the process comprising refining biomass under effective pretreatment conditions and refining conditions to generate a drilling fluid additive as disclosed. In some embodiments, the effective pretreatment conditions include the generation of lignosulfonic acids. Optionally, at least a portion of the lignosulfonic acids are not removed and remain present in the drilling fluid additive. In certain embodiments, the drilling fluid additive comprises a liquid slurry derived from the process. For example, the slurry may contain rheology modifiers derived from the biomass as well as water and pretreatment chemicals (such as acids, solvents, etc.).

Another application of these compositions is to use them as product enhancers of hydraulic fracturing fluids. Improvement in this purpose are particularly due to their impact in friction reduction, in improved pumping of proppants at a higher rate, at reduced pressure and predictable viscosity at high temperatures. Additionally, these products are fully biodegradable; they are produced from biomass, and are less susceptible to biofouling as could be other products like galactomannan derivatives.

Rheology modifiers may be crosslinked for robust gelling in fracking fluids. In some embodiments, crosslinking of rheology modifiers gives a stronger gel with more hydration.

Biomass-derived ash (from the biomass structure) or sand (from washing) may be used as a proppant, to displace mined silica.

The present invention, in other variations, provides fracturing fluid additives.

Some embodiments provide a fracturing fluid additive comprising rheology modifiers.

Some embodiments provide a fracturing fluid additive comprising rheology modifiers, wherein the additive further comprises lignosulfonates.

Some embodiments provide a fracturing fluid additive comprising rheology modifiers, wherein the additive further comprises non-sulfonated lignin.

Some embodiments provide a fracturing fluid additive comprising rheology modifiers, wherein the additive further comprises a crosslinking agent.

Some embodiments provide a fracturing fluid additive comprising crosslinked rheology modifiers and lignosulfonates.

Some embodiments provide a fracturing fluid comprising the fracturing fluid additive as disclosed. The fracturing fluid may be a water-based fracturing fluid, an oil-based fracturing fluid, or a hybrid water-based/oil-based fracturing fluid.

The fracturing fluid may further include, in addition to a disclosed fracturing fluid additive, one or more of a biomass-derived acid (such as acetic acid, formic acid, levulinic acid, and/or lignosulfonic acid), a biomass-derived corrosion inhibitor (such as lignin or a lignin derivative), a biomass-derived friction reducer (such as lignosulfonate or a lignosulfonate derivative), a biomass-derived clay-control agent, a biomass-derived crosslinking agent, a biomass-derived scale inhibitor, a biomass-derived breaker, a biomass-derived iron-control agent, a biomass-derived biocide (e.g., biomass hydrolysate), and/or a biorefinery-derived source of recycled or recovered water. Typically, the fracturing fluid carries, includes, or is intended to be combined with a proppant, which may be a biomass-derived proppant (such as ash contained in the structure of biomass and/or sand, ash, or dirt collected with biomass).

Some variations of the invention provide a method of using a fracturing fluid additive, the method comprising combining a disclosed fracturing fluid additive into a base fluid to generate a fracturing fluid. Some methods include introducing a fracturing fluid additive directly or indirectly into a geological formation.

In some variations, a process for producing a fracturing fluid additive comprises refining biomass under effective pretreatment conditions and refining conditions to generate a fracturing fluid additive as disclosed. In some embodiments, the pretreatment conditions include the generation of lignosulfonic acids, which optionally are not entirely removed and are present in the fracturing fluid additive. In some embodiments, the fracturing fluid additive comprises a liquid slurry derived from the process. For example, the slurry may contain rheology modifiers derived from the biomass as well as water and pretreatment chemicals (e.g., solvents, acids, bases, and so on).

The rheology modifiers of some embodiments are characterized by an average cellulose degree of polymerization from about 100 to about 2000, such as from about 400 to about 1200 or from about 500 to about 800. In certain embodiments, the rheology modifiers are free of enzymes.

The present disclosure is by no means limited to rheology modifiers. The material produced by the multiple refining steps (following biomass pretreatment) as disclosed, may be used in a wide variety of applications. For example, the rheology modifier may be incorporated into product selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a thickening agent, a rheological modifier, an additive for a drilling fluid, and combinations or derivatives thereof.

Some embodiments provide products with applications for sensors, catalysts, antimicrobial materials, current carrying and energy storage capabilities. Cellulose crystals have the capacity to assist in the synthesis of metallic and semiconducting chains.

Some embodiments provide composites containing refined cellulose and a carbon-containing material, such as (but not limited to) lignin, graphite, graphene, or carbon aerogels.

Cellulose crystals may be coupled with the stabilizing properties of surfactants and exploited for the fabrication of architectures of various semiconducting materials.

The reactive surface of —OH side groups in refined cellulose facilitates grafting chemical species to achieve different surface properties. Surface functionalization allows the tailoring of particle surface chemistry to facilitate self-assembly, controlled dispersion within a wide range of matrix polymers, and control of both the particle-particle and particle-matrix bond strength. Composites may be transparent, have tensile strengths greater than cast iron, and have very low coefficient of thermal expansion. Potential applications include, but are not limited to, barrier films, antimicrobial films, transparent films, flexible displays, reinforcing fillers for polymers, biomedical implants, pharmaceuticals, drug delivery, fibers and textiles, templates for electronic components, separation membranes, batteries, supercapacitors, electroactive polymers, and many others.

Other applications suitable to the present invention include reinforced polymers, adhesives, high-strength spun fibers and textiles, advanced composite materials, films for barrier and other properties, additives for coatings, paints, lacquers, adhesives, switchable optical devices, pharmaceuticals and drug delivery systems, bone replacement and tooth repair, improved paper, packaging and building products, additives for foods and cosmetics, catalysts, and hydrogels.

Aerospace and transportation composites may benefit from these rheology modifiers. Automotive applications include cellulose composites with polypropylene, polyamide (e.g. Nylons), or polyesters (e.g. PBT).

Rheology modifiers provided herein may be suitable as strength-enhancing additives for renewable and biodegradable composites. The cellulosic fibrillar structures may function as a binder between two organic phases for improved fracture toughness and prevention of crack formation for application in packaging, construction materials, appliances, and renewable fibers.

Rheology modifiers provided herein are may be as transparent and dimensional stable strength-enhancing additives and substrates for application in flexible displays, flexible circuits, printable electronics, and flexible solar panels. Cellulose is incorporated into the substrate-sheets are formed by vacuum filtration, dried under pressure and calandered, for example. In a sheet structure, cellulose acts as a glue between the filler aggregates. The formed calandered sheets are smooth and flexible.

Rheology modifiers provided herein may be suitable for composite and cement additives allowing for crack reduction and increased toughness and strength. Foamed, cellular cellulose-concrete hybrid materials allow for lightweight structures with increased crack reduction and strength.

Strength enhancement with cellulose increases both the binding area and binding strength for application in high strength, high bulk, high filler content paper and board with enhanced moisture and oxygen barrier properties. The pulp and paper industry in particular may benefit from rheology modifiers provided herein.

Porous cellulose may be used for cellular bioplastics, insulation and plastics and bioactive membranes and filters. Highly porous cellulose materials are generally of high interest in the manufacturing of filtration media as well as for biomedical applications, e.g., in dialysis membranes.

Rheology modifiers provided herein may be suitable as additives to improve the durability of paint, protecting paints and varnishes from attrition caused by UV radiation.

Rheology modifiers provided herein are suitable as thickening agents in food and cosmetics products. Rheology modifiers can be used as a thixotropic, biodegradable, dimensionally stable thickener (stable against temperature and salt addition). Rheology modifiers materials provided herein may be suitable as a Pickering stabilizer for emulsions and particle stabilized foam.

The large surface area of these rheology modifiers in combination with their biodegradability makes them attractive materials for highly porous, mechanically stable aerogels.

In some embodiments, the process comprises forming a structural object that includes the nanolignocellulose material, or a derivative thereof.

In some embodiments, the process comprises forming a foam or aerogel that includes the nanolignocellulose material, or a derivative thereof.

In some embodiments, the process comprises combining the nanolignocellulose material, or a derivative thereof, with one or more other materials to form a composite. For example, the other material may include a polymer selected from polyolefins, polyesters, polyurethanes, polyamides, or combinations thereof. Alternatively, or additionally, the other material may include carbon in various forms.

In some embodiments, the process comprises forming a film comprising the nanolignocellulose material, or a derivative thereof. The film is optically transparent and flexible, in certain embodiments.

In some embodiments, the process comprises forming a coating or coating precursor comprising the nanolignocellulose material, or a derivative thereof. In some embodiments, the nanolignocellulose-containing product is a paper coating.

In some embodiments, the nanolignocellulose-containing product is configured as a catalyst, catalyst substrate, or co-catalyst. In some embodiments, the nanolignocellulose-containing product is configured electrochemically for carrying or storing an electrical current or voltage.

In some embodiments, the nanolignocellulose-containing product is incorporated into a filter, membrane, or other separation device.

In some embodiments, the nanolignocellulose-containing product is incorporated as an additive into a coating, paint, or adhesive. In some embodiments, the nanolignocellulose-containing product is incorporated as a cement additive.

In some embodiments, the nanolignocellulose-containing product is incorporated as a thickening agent or rheological modifier. For example, the nanolignocellulose-containing product may be an additive in a drilling fluid, such as (but not limited to) an oil recovery fluid and/or a gas recovery fluid, or a fracturing fluid.

A nanolignocellulose-containing product may include any of the disclosed nanolignocellulose compositions. Many nanolignocellulose-containing products are possible. For example, a nanolignocellulose-containing product may be selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a thickening agent, a rheological modifier, an additive for a drilling fluid, and combinations or derivatives thereof.

Certain nanolignocellulose-containing products provide high transparency, good mechanical strength, and/or enhanced gas (e.g., $O_2$ or $CO_2$) barrier properties, for example. Certain nanolignocellulose-containing products containing hydrophobic nanocellulose materials provided herein may be useful as anti-wetting and anti-icing coatings, for example.

Some embodiments provide nanolignocellulose-containing products with applications for sensors, catalysts, antimicrobial materials, current carrying and energy storage capabilities.

Some embodiments provide composites containing nanolignocellulose and a carbon-containing material, such as (but not limited to) lignin, carbon black, graphite, graphene, or carbon aerogels.

The reactive surface of —OH side groups in nanolignocellulose facilitates grafting chemical species to achieve different surface properties. Surface functionalization allows the tailoring of particle surface chemistry to facilitate self-assembly, controlled dispersion within a wide range of matrix polymers, and control of both the particle-particle and particle-matrix bond strength. Composites may be transparent, have tensile strengths greater than cast iron, and have very low coefficient of thermal expansion. Potential applications include, but are not limited to, barrier films, antimicrobial films, transparent films, flexible displays, reinforcing fillers for polymers, biomedical implants, pharmaceuticals, drug delivery, fibers and textiles, templates for electronic components, separation membranes, batteries, supercapacitors, electroactive polymers, and many others.

Other nanolignocellulose applications suitable to the present invention include reinforced polymers, high-strength spun fibers and textiles, advanced composite materials, films for barrier and other properties, additives for coatings, paints, lacquers and adhesives, switchable optical devices, pharmaceuticals and drug delivery systems, bone replacement and tooth repair, improved paper, packaging and building products, additives for foods and cosmetics, catalysts, and hydrogels.

Aerospace and automotive applications include nanolignocellulose composites with polypropylene, polyamide (e.g. Nylons), or polyesters (e.g. PBT).

Nanolignocellulose materials provided herein are suitable as strength-enhancing additives for renewable and biodegradable composites. The cellulosic nanofibrillar structures may function as a binder between two organic phases for improved fracture toughness and prevention of crack formation for application in packaging, construction materials, appliances, and renewable fibers.

Nanolignocellulose materials provided herein are suitable as transparent and dimensional stable strength-enhancing additives and substrates for application in flexible displays, flexible circuits, printable electronics, and flexible solar panels. Nanolignocellulose is incorporated into the substrate-sheets are formed by vacuum filtration, dried under pressure and calandered, for example. In a sheet structure, nanocellulose acts as a glue between the filler aggregates. The formed calandered sheets are smooth and flexible.

Nanolignocellulose materials provided herein are suitable for composite and cement additives allowing for crack reduction and increased toughness and strength. Foamed, cellular nanolignocellulose-concrete hybrid materials allow for lightweight structures with increased crack reduction and strength.

Strength enhancement with nanolignocellulose increases both the binding area and binding strength for application in high strength, high bulk, high filler content paper and board with enhanced moisture and oxygen barrier properties. The pulp and paper industry in particular may benefit from nanolignocellulose materials provided herein.

Nanofibrillated cellulose nanopaper has a higher density and higher tensile mechanical properties than conventional paper. It can also be optically transparent and flexible, with low thermal expansion and excellent oxygen barrier characteristics. The functionality of the nanopaper can be further broadened by incorporating other entities such as carbon nanotubes, nanoclay or a conductive polymer coating.

Rojo et al., "Comprehensive elucidation of the effect of residual lignin on the physical, barrier, mechanical and surface properties of nanocellulose films," *Green Chem.*, 2015, 17, 1853-1866, is hereby incorporated by reference herein.

Porous nanolignocellulose may be used for cellular bioplastics, insulation and plastics and bioactive membranes and filters. Highly porous materials are generally of high interest in the manufacturing of filtration media as well as for biomedical applications, e.g., in dialysis membranes.

Nanolignocellulose materials provided herein are suitable as coating materials with oxygen barrier and affinity to wood fibers for application in food packaging and printing papers.

Nanolignocellulose materials provided herein are suitable as additives to improve the durability of paint, protecting paints and varnishes from attrition caused by UV radiation.

Nanolignocellulose materials provided herein are suitable as thickening agents in food and cosmetics products. Nanolignocellulose can be used as thixotropic, biodegradable, dimensionally stable thickener (stable against temperature and salt addition). Nanolignocellulose materials provided herein are suitable as a Pickering stabilizer for emulsions and particle stabilized foam.

The large surface area of these nanolignocellulose materials in combination with their biodegradability makes them attractive materials for highly porous, mechanically stable aerogels.

The present invention also provides systems configured for carrying out the disclosed processes, and compositions produced therefrom. Any stream generated by the disclosed processes may be partially or completed recovered, purified or further treated, and/or marketed or sold.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

EXAMPLES

Example 1: Nanolignocellulose Produced from Softwood

Softwood (pine) chips are processed in a pilot steam gun digester at a temperature of 185° C. and 20 minutes, resulting in a pulp yield of about 80%. The pulp is passed through a pilot plant disk refiner to defiberize the cooked chips to about 100 freeness. The freeness of pulp gives a measure of the rate at which a dilute suspension of pulp may be drained (see TAPPI T221 "Drainage Time of Pulp"). The pulp is then passed through a lab-scale homogenizer three times for a target of 80-85% fines, to produce unwashed nanolignocellulose. The percentage of fines (refined material) can be increased with more homogenizer passes. The unwashed nanolignocellulose is washed with water three times at 60° C. for 30 min at about 2, 1, and 1 kg water per kg pulp, to produce washed nanolignocellulose.

Figure 2:
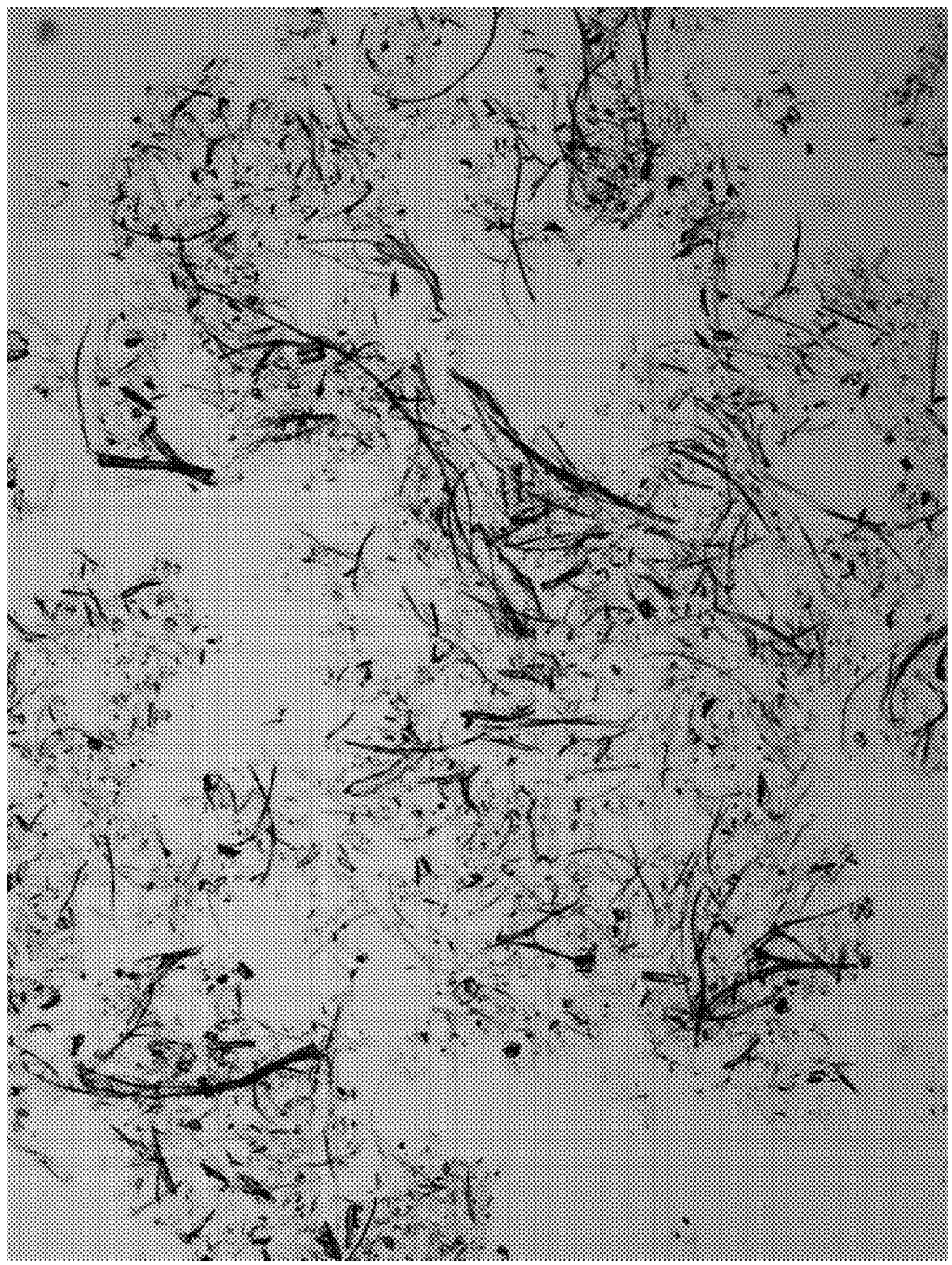
FIG. 2 is an optical micrograph at 40× magnification of washed nanolignocellulose produced in Example 1.

FIG. 2 shows an optical micrograph at 40× magnification of the washed nanolignocellulose produced in this example.

The nanolignocellulose in this example is a combination of precipitated lignin particles (with diameter of about 50 to 300 nanometers), lignocellulose nanofibrils (with lengths of about 500 nanometers, widths of about 10 to 500 nanometers, and lengths of tens of microns), and lignocellulose fines (with length <76 microns and width <5 microns).

The washed solids are analyzed for composition. The total carbohydrates are about 66.8 wt % of the solids. Glucan is 54 wt %, xylan is 9.2 wt %, galacatan is 1.3 wt %, arabinan is 0.6 wt %, and mannan is 1.7 wt %. The acetyl groups concentration is 1.9 wt % in the solids. Total lignin is 35.8 wt %, of which 33.3 wt % (on solids) is Klason lignin and 2.5 wt % (on solids) is acid-soluble lignin.

A liquid-phase analysis shows 0.98 wt % glucose, 7.44 wt % xylose, 0.42 wt % galactose, 0.35 wt % arabinose, and 0.79 wt % mannose, all sugars being a percentage on original total solids (% on wood). Formic acid is 0.07 wt %, acetic acid is 0.28 wt %, HMF is 0.02 wt %, furfural is 0.02 wt %, and dissolved lignin is 1.82 wt %, all again being a percentage on original total solids.

Example 2: Nanolignocellulose Produced from Hardwood

Hardwood chips are processed in a pilot steam gun digester at a temperature temperature of 185° C. and 15 minutes, resulting in a pulp yield of about 80%. The pulp is passed through a pilot plant disk refiner to defiberize the cooked chips to about 100 freeness. The pulp is then passed through a lab-scale homogenizer three times for a target of 80-85% fines, to produce unwashed nanolignocellulose. The percentage of fines (refined material) can be increased with more homogenizer passes. The unwashed nanolignocellulose is washed with water three times at 60° C. for 30 min at about 2, 1, and 1 kg water per kg pulp, to produce washed nanolignocellulose.

Figure 3:
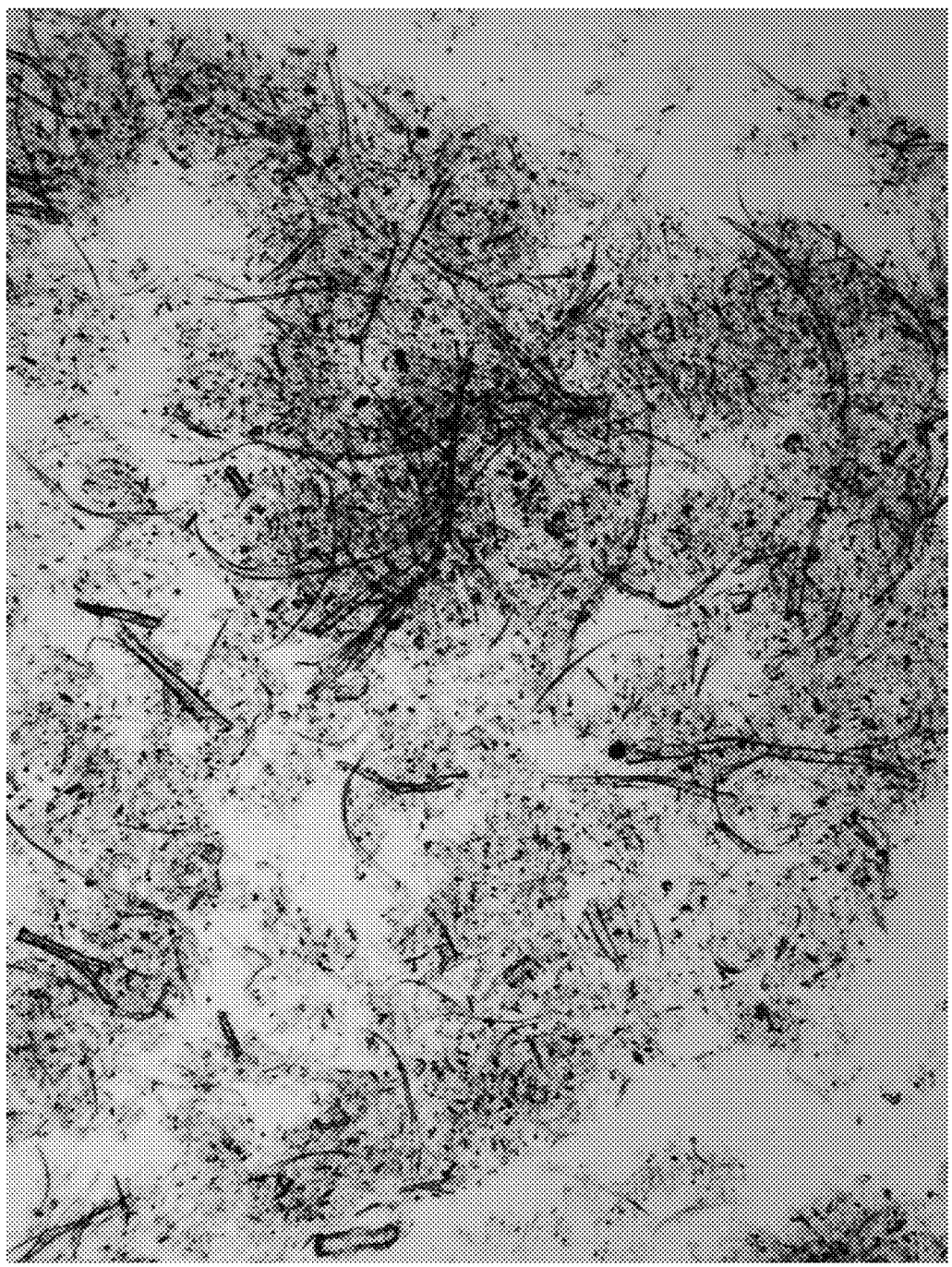
FIG. 3 is an optical micrograph at 40× magnification of washed nanolignocellulose produced in Example 2.

FIG. 3 shows an optical micrograph at 40× magnification of the washed nanolignocellulose produced in this example.

Figure 4:
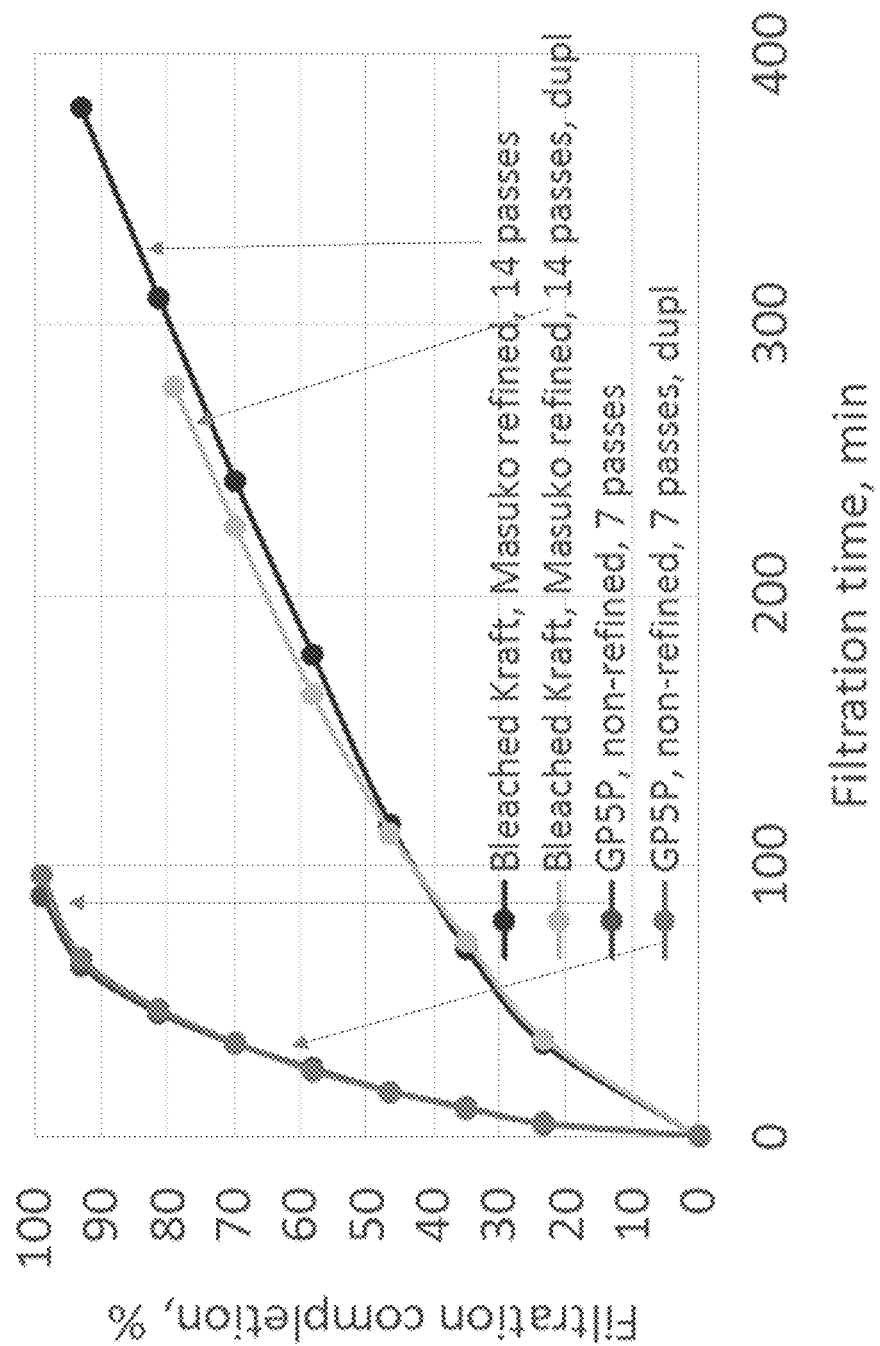
FIG. 4 is a graph of filtration rate of the Example 2 nanolignocellulose compared to prior-art Kraft pulp.

The pulp produced in this example is also passed through the homogenizer 7 times, resulting in 92% fines. This is compared to bleached softwood Kraft pulp, Masuko refined, 14 passes, 93% fines by area. FIG. 4 is a graph of filtration rate of this nanolignocellulose compared to prior-art Kraft pulp. Filtration is Buchner filtration at 0.8 wt % total solids, with a starting volume 450 mL (total available filtrate assumed to be 430 mL based on 17% total solids in the nanocellulose pad). Filter paper is Whatman 4 (pore size 20-25 μm).

FIG. 4 shows a considerably higher filtration rate for this nanolignocellulose versus bleached Kraft fibrils. In particular, the nanolignocellulose has essentially 100% filtration completion in less than 100 minutes. Because of high lignin content, the water retention value and drainage of the nanolignocellulose fibrils is much higher than pure cellulose fibrils. This is believed to be a key performance attribute for using nanolignocellulose on a paper machine.

What is claimed is:

1. A process for producing a nanolignocellulose composition, said process comprising:

(a) providing a lignocellulosic biomass feedstock;
(b) digesting said feedstock with a reaction solution including steam and/or hot water in a digestor under effective reaction conditions to produce a digested stream containing cellulose-rich solids, hemicellulose oligomers, and lignin;
(c) washing said cellulose-rich solids to separate at least a portion of said hemicellulose oligomers and/or at least a portion of said lignin from said cellulose-rich solids;
(d) mechanically treating said cellulose-rich solids to form a nanolignocellulose composition, wherein said nanolignocellulose composition comprises, on a bone-dry, ash-free, and acetyl-free basis, from about 35 wt % to about 80 wt % cellulose nanofibrils, cellulose microfibrils, or a combination thereof, from about 15 wt % to about 45 wt % lignin, and from about 5 wt % to about 20 wt % hemicelluloses, and wherein concentration of said cellulose nanofibrils and/or said cellulose microfibrils is calculated on a lignin-free, hemicellulose-free basis; and
(e) recovering said nanolignocellulose composition,
wherein said nanolignocellulose composition is characterized by an average nanoparticle diameter from about 3 nanometers to 100 nanometers and an average nanoparticle length from about 100 nanometers to about 10 microns, and
wherein said nanolignocellulose composition is characterized by at least 99% filtration completion in less than 100 minutes.

2. The process of claim 1, said process further comprising forming a pulp product or a paper product containing said nanolignocellulose composition.

* * * * *